(12) United States Patent
Granier (10) Patent No.: US 6,595,978 B2
(45) Date of Patent: Jul. 22, 2003

(54) INJECTION SYRINGE, COMPRISING SUCTION MEANS

(75) Inventor: Patrick Granier, Mazamet (FR)

(73) Assignee: SOFIC, Mazamet (FR)

( * ) Notice: Subject to any disclaimer, the term of this patent is extended or adjusted under 35 U.S.C. 154(b) by 0 days.

(21) Appl. No.: 09/997,251

(22) Filed: Nov. 30, 2001

(65) Prior Publication Data

US 2002/0103471 A1 Aug. 1, 2002

Related U.S. Application Data (60) Division of application No. 09/456,320, filed on Dec. 8, 1999, now abandoned, which is a continuation-in-part of application No. PCT/FR98/01171, filed on Jun. 9, 1998.

(30) Foreign Application Priority Data

Jun. 9, 1997 (FR) .............................................. 97 07097

(51) Int. Cl.$^7$ .............................................. A61M 31/00
(52) U.S. Cl. ..................... 604/506; 600/578; 604/133
(58) Field of Search ................................ 604/181, 187, 604/195, 197, 210, 232, 415, 411, 412, 413, 131, 152, 156, 86, 82, 85, 133, 87–91, 135, 200–205, 134, 139; 600/562–584

(56) References Cited

U.S. PATENT DOCUMENTS 5,180,371 A * 1/1993 Spinello ..................... 604/118
5,281,198 A * 1/1994 Haber et al. ................... 604/86
5,354,284 A * 10/1994 Haber et al. ................. 604/191
5,456,678 A * 10/1995 Nicoletti ..................... 604/413
5,637,094 A * 6/1997 Stewart, Jr. et al. ........ 604/135

* cited by examiner

Primary Examiner—Brian L. Casler
Assistant Examiner—Jennifer Maynard
(74) Attorney, Agent, or Firm—Lowe Hauptman Gilman & Berner, LLP (57) ABSTRACT

The invention concerns a disposable injection syringe, in particular in the field of dentistry, comprising: a syringe body provided with a needle at one first end thereof, the needle comprising an external part extending outside the body and an internal part extending inside the body, the needle forming an end external to the body and an end internal to the body; means for grasping the syringe body, at a second end thereof opposite the first end; a mobile injection rod; a cartridge containing a product to be injected, arranged inside the body between the needle internal end and the body second end in an inoperative position, the cartridge capable of being moved from the inoperative position towards the body first end under the injecting rod pressure; elastic means for automatically returning the cartridge towards the inoperative position when the pressure on the injecting rod is released, to cause a depression in the cartridge.

3 Claims, 5 Drawing Sheets

INJECTION SYRINGE, COMPRISING SUCTION MEANS

RELATED APPLICATION

The present application is a division of application Ser. No. 09/456,320 filed Dec. 8, 1999 now abn, which is a continuation and claims priority from PCT Application No. PCT/FR98/01171 filed Jun. 9, 1998, the disclosures of which are incorporated by reference herein in its entirety.

BACKGROUND OF THE INVENTION

1. Field of the Invention

The present invention relates to injection syringes, devices and modules, of the type for single use, especially but not exclusively for the field of dentistry.

2. Description of Related Art

Such syringes are known from manufacturers of these materials, practitioners and patients and generally comprise a body provided with a needle at a first end of the former, the needle comprising an external portion extending outside the body and an internal portion extending inside the body, the needle forming thus an end external to the body and an end internal to the body, means for grasping the body of the syringe, at a second end of the latter opposite the first end, a mobile injection rod, a detachable cartridge containing a product to be injected, disposed inside the body between the internal end of the needle and the second end of the body in an inoperative position, this cartridge being capable of moving from the inoperative position towards the first end of the body under the pressure of the injection rod, during an injection.

The devices mentioned above are made up of the syringes described below, thus intended to function in conventional manner in co-operation with a cartridge pre-filled with a product to be injected, but are marketed without this cartridge in order to allow the practitioner to introduce into it the cartridge of his choice, depending on his needs.

The modules also mentioned above are made up of a portion of the devices described above, which can be marketed without the grasping means and without the injection rod, the latter then being constituted by detachable and reusable grasping means and rod, which the user can have available, only the module (and the cartridge) being in this case for single use and disposed of after use.

Such syringes, devices and modules function perfectly. However, as is known in the field of dentistry especially, the practitioner who has to carry out an injection of anaesthetic products for example, must be assured that the external end of the syringe does not open into a blood vessel of the oral cavity. For this, the practice consists in operating slight suction by means of the injection syringe in order to check that blood does not come to color the product to be injected, if necessary.

This operation, carried out when the needle has penetrated the flesh, necessitates a delicate and hardly practical maneuver with the devices of prior art, by precisely measured traction applied to the injection rod whilst keeping the body immobile, which traction must not be too strong in order to avoid the possible introduction of too large a quantity of blood if necessary, but sufficient to make it possible to ensure verification in a certain manner.

There is known, especially through the French application no. 2,696,096, a syringe making it possible to improve the suction operation by introducing a "damper" for the displacement of the rod, as it were. This application teaches a syringe comprising a rod fitted at one end with a head complementary in cross-section to the internal cross-section of the cartridge, said head being intended to rest on the mobile plug of the cartridge to permit the expulsion of the product outside the latter via the injection needle, this head being capable of sliding on the internal walls of the cartridge and presenting an escape conduit connecting the volume delimited between the head and the plug to the exterior of the cartridge, this escape conduit having a significant loss of load.

Thus the air imprisoned in a first period of time in the above volume is expelled via the escape conduit, in such a way as to permit the head to come into contact with the plug. In a second period of time, the user, via weak traction exercised on the rod, is going to move the head over a short distance in the direction of the position before use; the plug still adhering momentarily to the internal wall of the cartridge, a partial vacuum is then going to be created between the head and the plug, in such a way as to constrain the latter to leave its position and to come into contact with the head again. Displacing the plug in the direction of its position before use is thus going to generate a slight suction phenomenon, sufficient in any case to permit the possible introduction of several drops of blood into the cartridge if need be.

This device, which functions perfectly and significantly improves the prior devices necessitating a complex maneuver of the rod by combined rotation and traction, nevertheless requires the practitioner to exercise traction in order to create a suction phenomenon.

Document WO 94/16752 is known which relates to a self-injection device having a tubular sleeve in which is axially arranged a cartridge closed at its front end by a membrane and at its rear end by a piston. An injection needle is fitted sliding axially in the cartridge. A tubular actuating cap, secured against removal, is guided sliding on the rear end of the sleeve and makes it possible to actuate the device via a rod which acts on the piston and extends from the bottom of the cap into the sleeve. This device comprises, between the membrane of the sleeve and a shutter, placed in the sleeve and carrying the needle, a protective cap intended to keep a portion of the needle in sterile conditions, and a spacer spring, the function of which is to keep the cartridge at a distance from the internal end of the needle in order to avoid accidental piercing of the membrane, whilst allowing its compression to permit the device to function. In an alternative manner, the functions of the protecting cap and the spacer spring can be combined in the same part.

SUMMARY OF THE INVENTION

The object of the present invention is to propose injection syringes, devices and modules of the type for single use, making it possible to overcome the disadvantages of known syringes, devices and modules, and making it possible for, the practitioner to carry out the suction operation without having to apply traction to the injection rod, whilst proposing systems which are simple in conception and practical to use.

Another object of the present invention is to propose injection syringes, devices and modules of the type for single use, making possible minimal sterile packaging, and advantageously without wrapping up the syringe body.

Another object of the present invention is to supply injection syringes, devices and modules of the type for single use which permit, thanks to the suction without traction, a reduction in the sterile packaging of the proposed injection syringes, devices and modules.

Another object of the present invention is to propose injection syringes, devices and modules of the type for single use, at modest costs compatible in particular with the intention of single use of these products.

Another object of the present invention is to propose injection syringes, devices and modules of the type for single use, providing for the user and for third parties, excellent security against accidental pricking with the injection needle.

To this end, the present invention consists of an injection syringe of the type for single use, especially for the field of dentistry, comprising:

syringe body fitted with a needle at a first end of the former, said needle comprising an external portion extending outside said body and an internal portion extending inside said body, said needle forming an end external to said body and an end internal to said body, means for grasping said syringe body, at a second end of the latter, opposite said first end, a mobile injection rod, a cartridge containing a product to be injected, disposed inside said body between said internal end of the needle and said second end of the body in an inoperative position, said, cartridge being capable of moving from the inoperative position towards said first end, of the body under the pressure of the injection rod elastic means for automatically returning the cartridge towards said inoperative position when the pressure on said injection rod is released, in order to cause a depression in said cartridge, characterized in that said elastic means are disposed inside said body between the first end of the letter and said cartridge, and in that said elastic means are formed by a flexible tubular envelope surrounding said internal portion of the needle.

Thanks to a return induced by the elasticity of, an appropriate material, the elastic means, as defined above, allow the user to be spared any traction force in order to carry out the suction operation, necessary to check that the needle is not placed in a blood vessel. Thus the practitioner only has to apply force in a single direction when carrying out an injection, whether this be for the injection itself of the product, or for the suction operation. Indeed, when the practitioner wants to check if the external end of the needle has penetrated a blood vessel, he only has to release the pressure exercised on the injection rod, the elastic means then returning the cartridge towards the inoperative pre-injection position, thus causing a depression in the cartridge itself, therefore sucking up the blood via the end of the needle engaged in a blood vessel, if need be, According to another advantageous characteristic, said elastic means are guided by said internal portion of the needle.

According to another advantageous characteristic, the syringe according to the invention to comprises detachable means of covering at least the external portion of the needle, these means being intended to be removed before the injection, and said flexible tubular envelope covers said internal portion of the needle in such a way as to define a sterile space enclosing the needle, inside the flexible tubular envelope and the covering means.

This characteristic makes it possible to avoid sterile packaging of the complete syringe and to confine the needle alone in a sterile environment, which further reduces the costs of the sterile packaging. The double function played by the tubular envelope in this case will be noted.

According to another advantageous characteristic, the syringe according to the invention comprises a protective sheath moveable along said syringe body, between two extreme positions, one of which permits covering said external portion of the needle and the other the disengagement of the external portion of the needle.

This characteristic provides excellent security for the practitioner and third parties against accidental pricking with the soiled needle after injection. Indeed, once the injection has been carried out, the practitioner places the sheath in a position covering the external portion of the needle, thus avoiding anybody accidentally pricking himself whilst manipulating the syringe.

The invention will be better understood, and other characteristics and advantages will appear in reading the following description of an embodiment of a syringe, a device and a module according to the invention, accompanied by the attached drawings, these examples being given by way of illustration and without any restrictive interpretation of the invention being able to be taken from them.

DETAILED DESCRIPTION OF THE PREFERRED EMBODIMENTS

Figure 1:
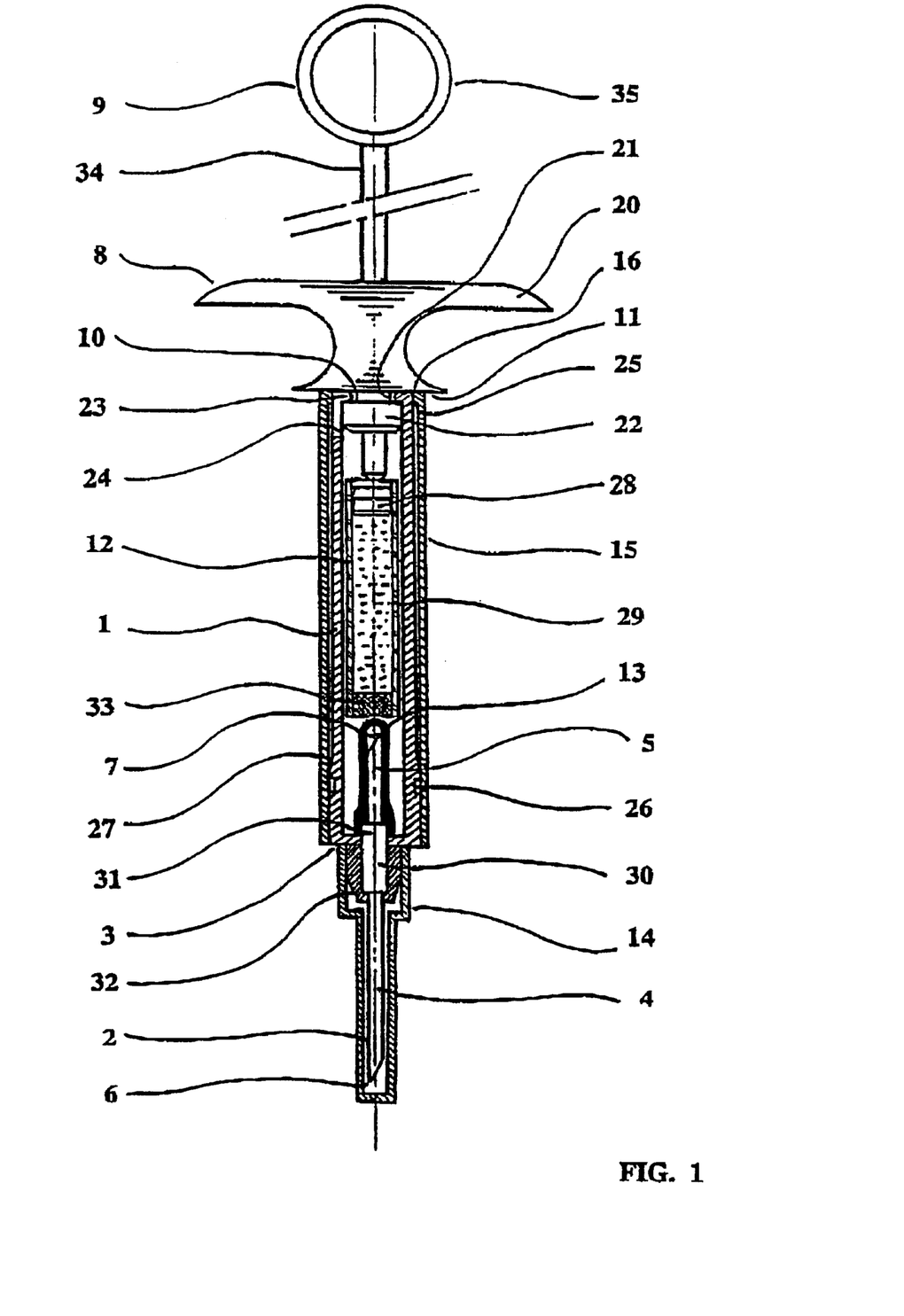
FIG. 1 represents a view in partial longitudinal section and in an inoperative position, before injection, of an embodiment of a syringe according to the invention.
Figure 2:
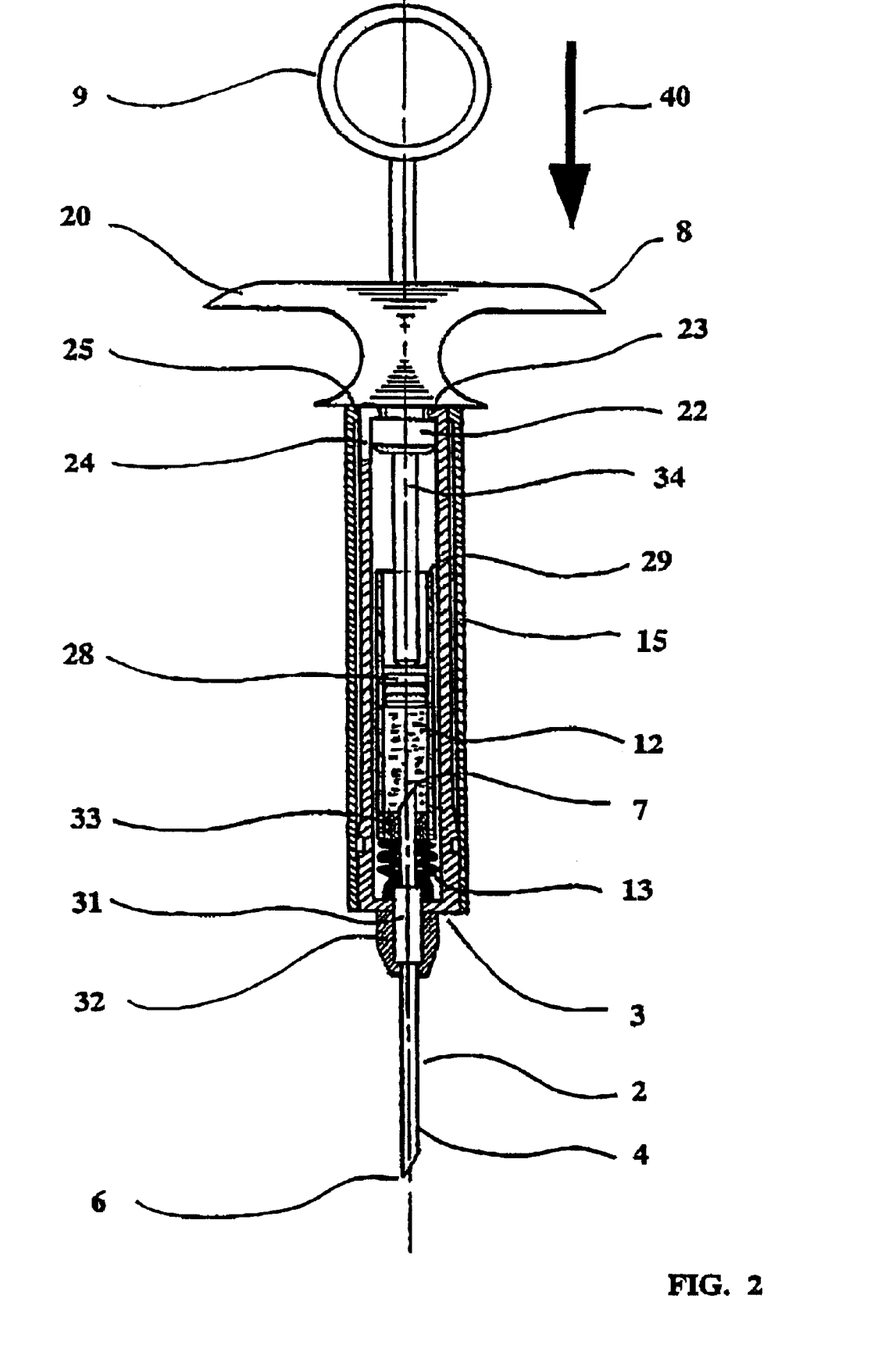
FIG. 2 represents a view in longitudinal section and in an operating position, during an injection, of the example of FIG. 1.
Figure 3:
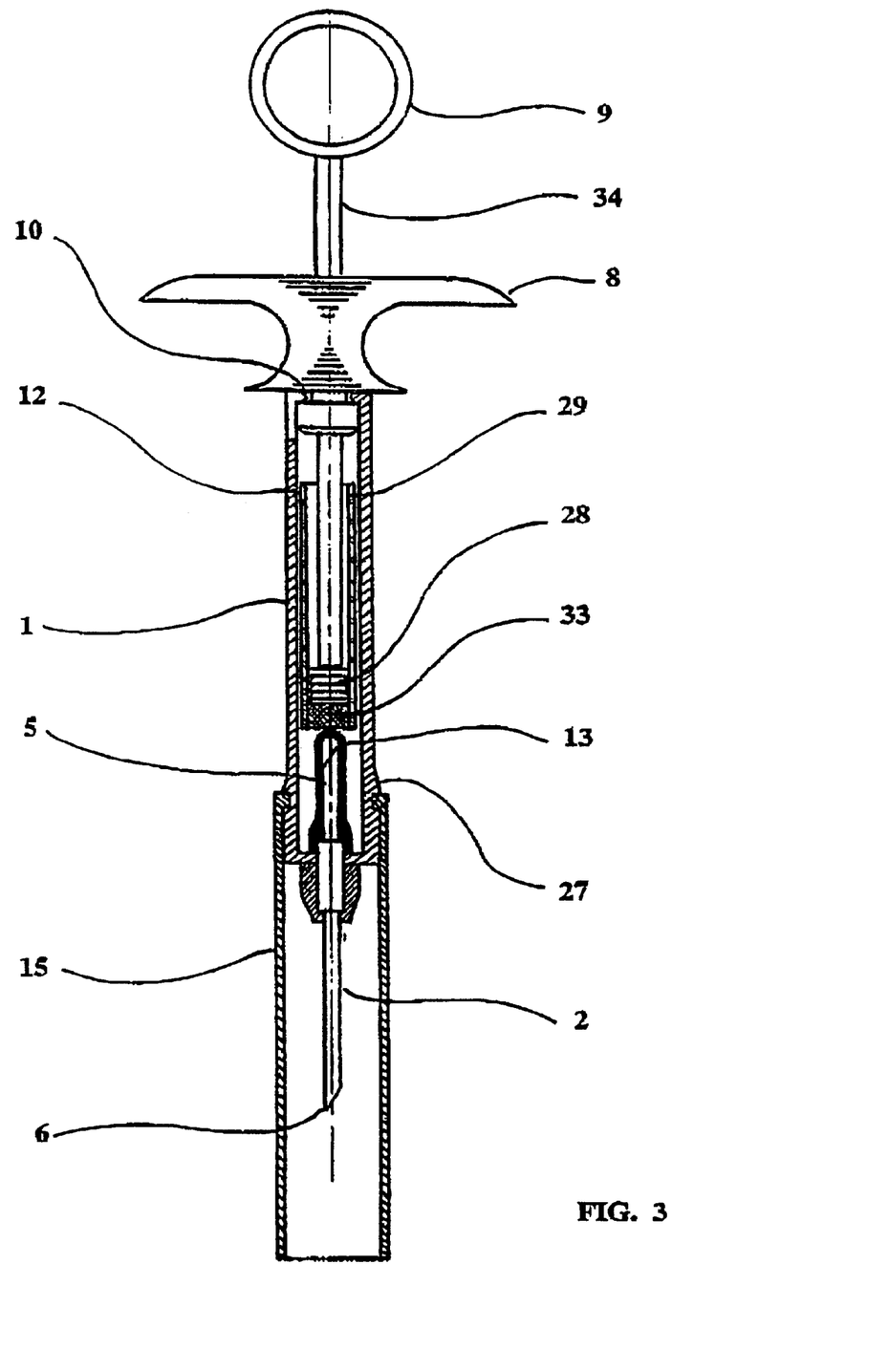
FIG. 3 represents a view in longitudinal section, after injection, of the example of FIG. 1.

The syringe represented on FIGS. 1, 2 and 3 comprises, in known manner, a tubular syringe body 1, for example of circular cross-section, in an advantageously transparent plastics material, fitted with a needle 2 at a first end 3 of the syringe body, the needle 2 comprising an external portion 4 extending outside the body 1 and an internal portion 5 extending inside the body 1, and forming an end 6 external to the body 1 and an end 7 internal to the body 1, means fox grasping 8 the syringe body 1 at a second end 11 of the latter opposite the first end 3, a mobile injection rod 9, a cartridge 12 containing a product to be injected, disposed inside the body 1 between the internal end 7 of the needle 2 and the second end 11 of the body 1, in an inoperative position, the cartridge 12 being capable of moving from the inoperative position towards the first end 3 of the body 1 under the pressure of the injection rod 9, and comprises according to the invention elastic means 13 for automatically returning the cartridge 12 towards the inoperative position when the pressure on the injection rod 9 is released.

The grasping means are advantageously removable from the syringe body 1 and are formed by a support element 8 of any appropriate known shape, for example such as that represented on FIGS. 1–4, intended to be assembled on the body 1 via housing 10 at the second end 11 of body 1 after the introduction of the cartridge 12 into the body 1.

A housing 10 can be realized by means of a cylindrical part 22 formed on the support element 8 as represented on FIG. 1, for example, the cylindrical part 22 having an external diameter substantially equal to the internal diameter of the body 1, and intended to be introduced into the syringe body 1 in order to produce guiding and centering of the support element 8 on the body 1, of the second end of the body 1 into which the cylindrical part 22 penetrates, of an annular throat 21 formed in the cylindrical part 22, and of an annular rib 23 complementary in shape to throat 21 realized on the cylindrical internal surface of the body 1 at its second end 11, the annular rib 23 being intended to penetrate into throat 21 during the introduction of the cylindrical part 22 of the support element 8 into the body 1, and thus associate the latter with the body, as represented in FIGS. 1, 2 and 3.

In order to facilitate the introduction of the cylindrical part 22 into the body 1 of the syringe, for example two or three grooves 24 are realized in the body 1 in a longitudinal. manner at its second end 11, the grooves 24 separating the rib into two or three distinct sectors. The grooves 24 make it possible to spread out the lips thus created at the second end of the body 1, during the passage of the cylindrical part 22, the lips re-gripping around the cylindrical part 22 as a result of their elasticity once the throat 21 is in the plane of the rib 23, advantageously when grasping means abut on the end of the body.

The syringe represented on FIGS. 1, 2 and 3 comprises advantageously a protective sheath 15 moveable along the syringe body 1 between two extreme positions, of which the one represented on FIG. 3 permits covering of the external portion 4 of the needle 2 and the other, represented on FIGS. 1 and 2, the disengagement of the external portion 4 of the needle 2.

The protective sheath 15, in the disengaged position of the external portion 4 of the needle 2 advantageously serves as means for locking 16 the housing 10. The sheath 15 is provided at one end with an internal collar 25, the internal diameter 16 of which is slightly lower than the external diameter of body 1 in such a way as to keep the second end of the body supported on the cylindrical part of the support element 8 and to prevent any spreading of the lips of the second end 11 of the body 1, and the release of the housing 10 for example under the effect of forces created by the movement of rod 9 during an injection.

The collar 25 is also intended to co-operate with an annular throat 26 realized on the external surface of the body 1 and towards its first end 3, as represented on the figures, in order to permit the immobilization of the sheath in a position covering the external portion 4 of the needle 2 after the injection has been carried out, as represented on FIG. 3, the collar 25 coming to lodge itself in the annular throat 26. In this position, the sheath 15 should no longer be able to change position, at any rate according to normal forces, and the body 1 will comprise advantageously, in order to facilitate the penetration of the collar 25 into the throat 26, an annular slope 27 like a flattened cone intended to draw out the collar 25, in an elastic manner, before the latter retracts within the throat 26 under the effect of the elasticity of the material composing same, which will be by preference a transparent plastics material. Body 1 will be able to comprise also, in order to facilitate the placing of the sheath 15 in a position covering the external portion of the needle 2, longitudinal slits (not represented? realized in the zone of the slope 27 and/or the throat 26.

The sheath 15 will be of sufficient length to cover completely the external portion 4 of the needle 2 when the collar 2 is engaged in the throat 26.

The grasping means will be of an advantageously constant width, substantially equal to the external diameter of the protective sheath 15.

The injection rod 9 is formed from a spindle 34 which is guided in its movements of translation and rotation by the grasping means 8, with the aid of a bore realized in the latter and in which the spindle 34 is adjusted sliding. One end of the spindle 34 is fitted, for example, with an integral maneuvering ring 35, and its other end can be provided with any appropriate element or shape depending on the cartridge piston on which it is intended to zest. A shape of a simple support surface, ensuring the necessary transmission of the forces necessary to displace the piston with a view to evacuating the contents of the cartridge, is sufficient in the case of the syringe according to the invention, as represented on FIGS. 1 to 3.

The cartridge 12 is presented in the form of a known cartridge as currently used in syringes' for use in dentistry in particular. The cartridge 12 is made up of a tube 29 in a rigid transparent material fitted at one end with a piston 28 capable of moving inside the tube 29 in order to evacuate the contained liquid via the other end of the tube 29 which is fitted with a fixed impermeable plug 33, intended to be pierced by the interior portion 5 of the needle 2 when the cartridge is displaced in the syringe body, from its second end 11 towards its first end 3 under pressure of the syringe rod 9 for the purposes of an injection. The cartridge 12 is introduced into the syringe body 1 via the first end of the latter, The body 1 is fitted at its first end with a needle 2, associated with the former by any known means, for example by gluing, welding or the like, and advantageously with the aid of a rigid sleeve 30, one end 31 of which emerges inside the body 1, as represented on FIGS. 1 to 3, on which end 31 the elastic means for automatically returning the cartridge 12 will be fixed, as will be explained below.

The first end 3 of the body 1 will be fitted with an end piece 32 surrounding the portion of the sleeve 31 external to the syringe body 1, and will be ,intended with the end piece 32 to cooperate with detachable means for covering 14 at least the external portion 4 of the needle 2, with a view to confining the latter in a sterile space until the detachable covering means 14 are withdrawn to carry out the injection. The detachable covering means will take the form of an impermeable cap 14, for example in a plastics material, of which one open end has an internal shape complementary to the external shape of the end piece 32 of the body 1, on which the cap 14 is intended to be fitted as a force fit, as represented on FIGS. 1 and 5.

The elastic means are advantageously disposed inside the body 1 between the first end 3 of the latter and the cartridge 12, and are made up of a flexible tubular envelope surrounding the internal portion 5 of the needle 2, as represented on FIGS. 1 and 3. The tubular envelope 13 will preferably be realized in an elastic material such as natural or synthetic rubber, having good elasticity properties in order to allow automatic return of the cartridge towards the end of the syringe body 1 once the pressure on the syringe rod 9 is released.

The tubular envelope 13 will preferably be impermeable, and will cover the internal portion 5 of the needle 2, in such a way as to define a sterile space enclosing the needle 2, inside the flexible tubular envelope and the covering means 14. The envelope 13 is advantageously fixed on the portion of the sleeve 30 emerging inside the body 1, as represented on FIGS. 1 to 3, by means of a force fit using the elasticity of the envelope 13 in order to grip tightly the emerging portion of the sleeve 30. The envelope 13 is put into place by pressure on the latter whilst guarding against perforating it on the internal end 7 of the needle 2.

FIGS. 1, 2 and 3 show the position of the cartridge 12 and of the piston 28 of the latter, respectively before use of the syringe ready for an injection, in the course of injection, and after the injection, the operator having manually placed the sheath 15 in the position covering the external portion of the needle 2.

The means for automatically returning the cartridge function as follows:

- envelope 13, before the syringe is used, as represented on FIG. 1, advantageously permits, in addition to the sterile containment of the needle, the formation, between the cartridge and the internal end 7 of the needle, of a shock-absorbing film preventing any accidental perforation of the impermeable plug 33 of the cartridge 12 during manipulation or transportation of the syringe;
- under pressure of the syringe rod 9, represented by arrow 40 on FIG. 2, the cartridge 12 moves towards the first end 3 of the syringe body 1, and the internal end 7 of the needle 2 makes an incision in the envelope 13 and the impermeable plug 33 of the cartridge 12. Envelope 13 then abuts between the cartridge 12 and the end 3 of the body 1 or the sleeve 30, and any new pressure, or continuous pressure, on the rod 9 will compress the envelope 13 which, in its displacement by compression, is guided by the internal portion 5 of the needle 2, as represented on FIG. 2;
- as soon as the pressure on the rod 9 is released, the energy potential stored up by the compressed envelope 13 is released and permits the movement of the cartridge 12 of the rod 9 towards its initial position, creating a suction inside the cartridge 12, thus provoking suction by the external end 6 of the needle 2. Care will be taken to ensure that the interior portion 5 of the needle 2 is sufficiently long to permit displacement of the cartridge 12, necessary for sufficient suction to introduce a small quantity of blood into the cartridge 12 if need be. The operator advantageously controls, by appropriate immobilization of the rod 9, the amount of movement of the cartridge 12 towards its initial position;
- once the injection is finished, the envelope 13 automatically and advantageously returns the cartridge to its initial position, as represented on FIG. 3, under the effect of the energy stored up during the injection. Under the effect of its own elasticity, the envelope 13 substantially reassumes its initial pre-injection shape, the incision created for the injection closing of its own accord through the joining of the envelope lips. The internal portion of the needle is thus completely covered after the injection, giving the syringe according to the invention increased safety; similarly, if, during the injection, the cartridge should become detached from the internal portion 5 of the needle 2, for example by complete relaxation of the pressure on the rod 9, the envelope 13 would immediately cover the latter as a result of its elasticity, as explained above, preventing any contamination of the needle by the external environment.

It should be noted that the grasping means 8, which are advantageously removable in the single-use type of embodiment of the syringe according to the invention, can also be fixed in a non-removable manner to the syringe body, as is the case in known syringes in which the cartridge is introduced into the syringe body via a window at the side of the body.

Figure 4:
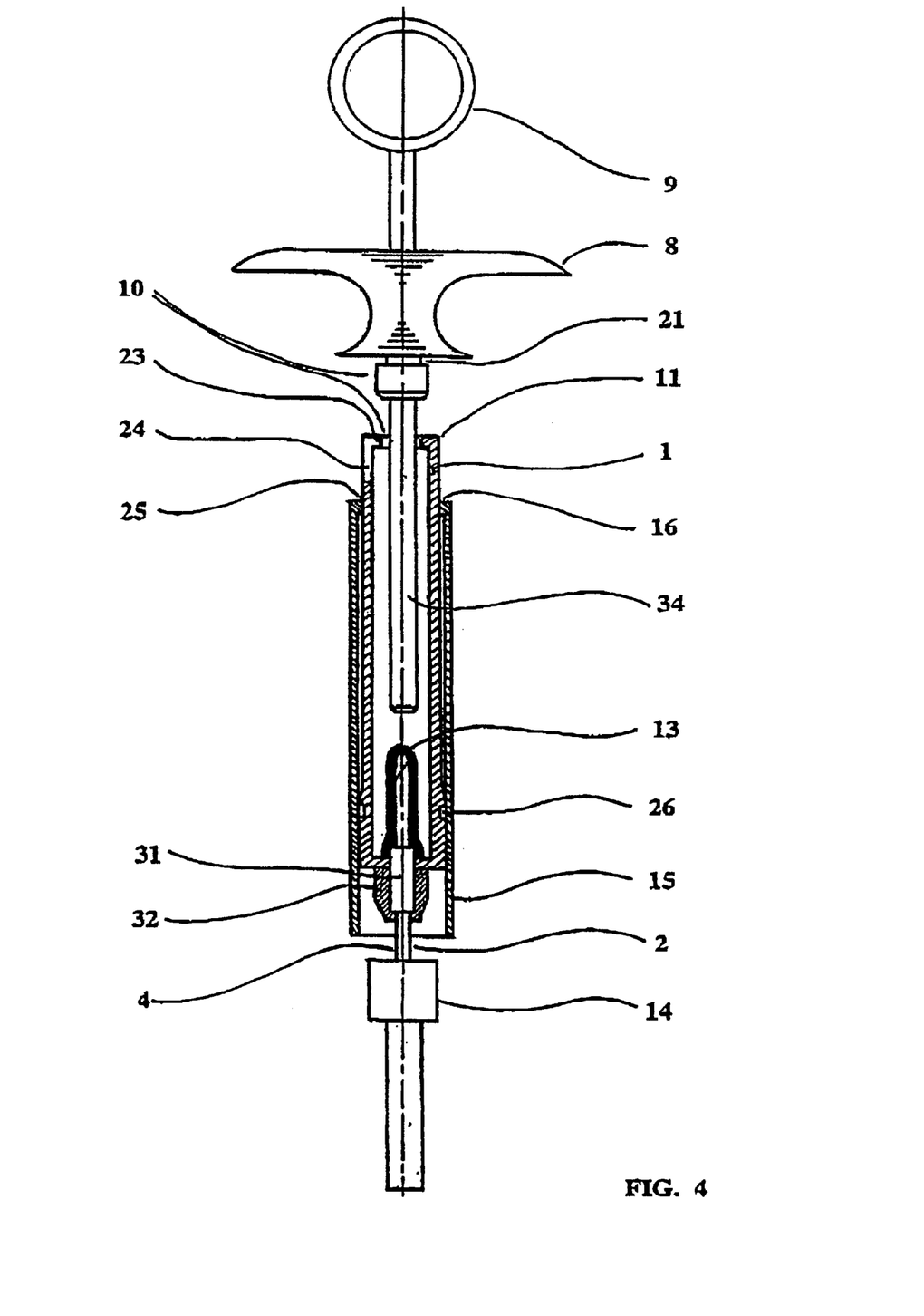
FIG. 4 represents a view in partial longitudinal section, and exploded, of an embodiment of a device according to the invention.

FIG. 4 represents an embodiment of an injection device for single use according to the invention, identical in every respect to the syringe according to the invention described with the aid of FIGS. 1 to 3, but from which the cartridge 12 has been removed. The reference numerals used for the elements of the device are identical to those used for the same elements of the syringe. Such a device is packaged without a cartridge, the user or distributor introducing the cartridge of his choice.

On FIG. 4, the grasping means 8 with the rod 9 crossing them free in translation and in rotation, have been represented not-assembled on the syringe body 1. The cap 14 has also been represented on FIG. 4 not associated with the body 1, and the sheath 15 has been represented in a position providing housing for the grasping means 8 on the syringe body 1, as explained above with the aid of FIGS. 1 to 3.

It will be noted that, when the cap 14 is in place on the end piece 32, on the syringe as on the device according to the invention, the needle 2 is confined within a closed space, advantageously sterile, making it possible to avoid expensive and unnecessary packaging of the whole device or the whole syringe, for example in sterile, impermeable wrapping.

In order to be in a pre-injection condition of use, the device represented on FIG. 4 should undergo the following operations; introduction of a cartridge (not represented) into the body 1 via its second end 11; positioning of the grasping means 8 and the rod 9 on the second end 11 of the body 1; placing the sheath 15 in its position disengaged from the external portion 4 of the needle 2 in order especially to lock the grasping means on the body 1; and withdrawal of the cap 14.

Figure 5:
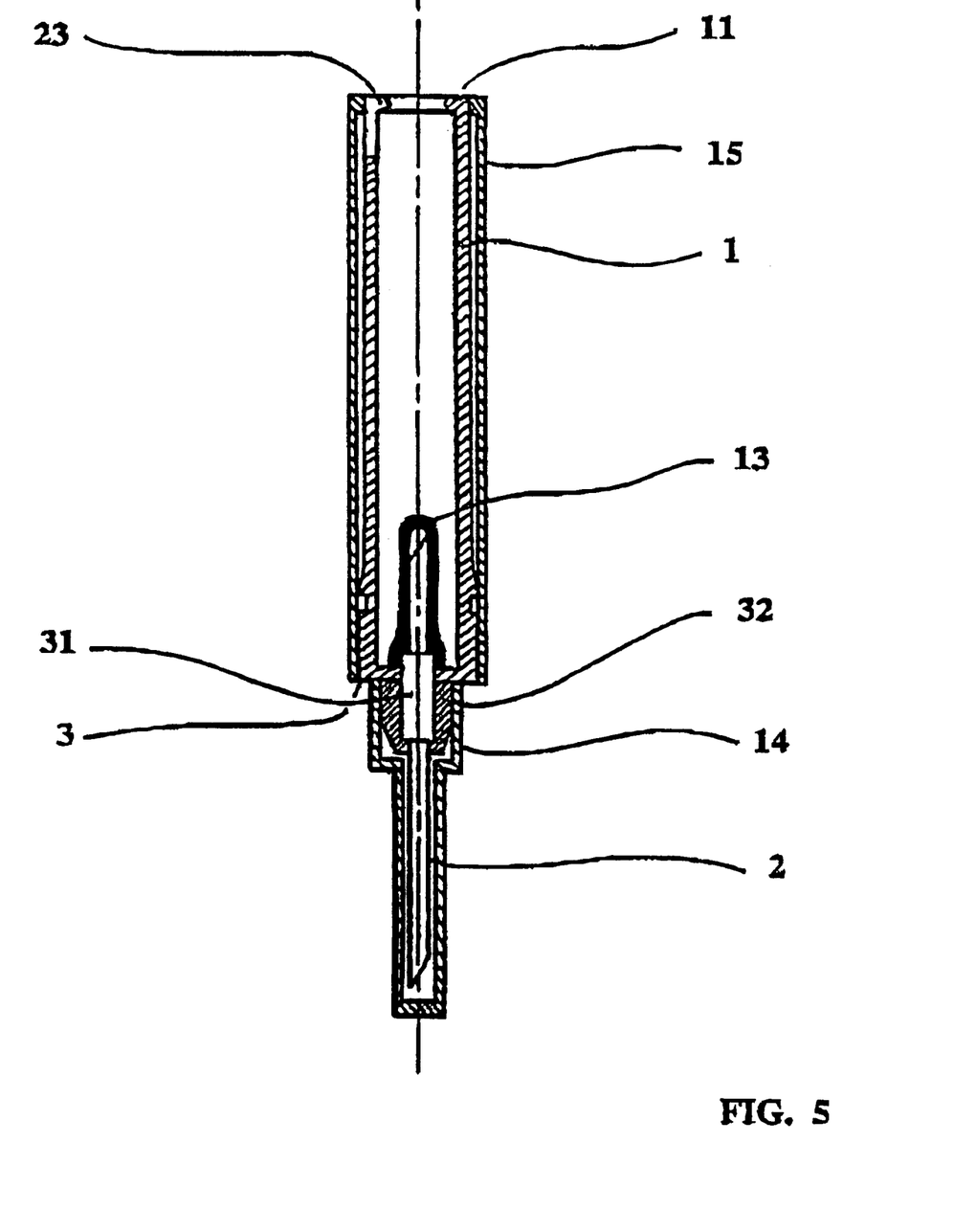
FIG. 5 represents a view in longitudinal section of an embodiment of a module according to the invention.

FIG. 5 represents an embodiment of an injection module for single use according to the invention, identical in every respect to the device according to the invention described with the FIG. 4, but from which the grasping means and the injection rod have been removed. The reference numerals used for the elements of the module are identical to those used for the same elements of the device. Such a module is packaged without grasping means and without injection rod, the user or the distributor being able to use the reusable grasping means and injection rod of his choice.

On FIG. 5, the module has been represented as packaged for use or distribution. It will be noted that, as for the device, complete packaging of the module is avoided by confinement of the needle 2 in a sterile space inside the flexible tubular envelope 13 and covering, means 14.

The interest of the module according to the invention is in permitting the possible reduction of the costs of a syringe according to the invention, by avoiding manufacturing grasping means and an injection rod for each module produced, the user having available in this case appropriate grasping means and an appropriate rod, for example made of stainless steel and therefore reusable.

In the case of the device according to the invention, the grasping means and the injection rod are intended for single use and are manufactured in an inexpensive material, in a plastics material for example.

What is claimed is:

1. A method of carrying out a suction operation with a syringe comprising:
    inserting a cartridge into a syringe body; wherein the syringe body comprises:
        a first end;
        a second end opposite to said first end; and
        a needle at said first end, said needle comprising:
            an external portion extending outside said body and terminating in a first needle end; and
            an internal portion extending toward said second end of said body inside said body and terminating in a second needle end inside said body;

means for grasping said syringe body proximate to said second end of said syringe body; and a mobile injection rod in operative association with said grasping means and said cartridge;

wherein said cartridge, containing a product to be injected, is disposed inside said body between said internal end of the needle and said second end of the body in inoperative position and is adapted to be moved from said inoperative position spaced from the second needle end of said internal portion of said needle, toward said first end of the body under die pressure of the injection rod; and elastic means disposed inside said body between the first end of the same and said cartridge;

said method further comprising:

exerting pressure on said mobile injection rod whereby causing said cartridge to move from said inoperative position into compressive contact with said elastic means, causing said second needle end to be introduced into said cartridge, and penetrating an object with the first needle end; and releasing said pressure on said mobile injection rod whereby causing said cartridge to move toward said inoperative position under elastic force of said elastic means, causing a suction to be drawn inside said cartridge via said needle, and causing material to be drawn from said object into said cartridge.

2. A method as claimed in claim 1 wherein said object is animal flesh.

3. A method as claimed in claim 2 wherein said animal is human.

* * * * *